United States Patent [19]

Wilkinson et al.

[11] 4,110,432

[45] Aug. 29, 1978

[54] CONJUGATES OF PROSTAGLANDINS, ANALOGS, FORMULATIONS AND THEIR USE

[75] Inventors: Samuel Wilkinson, Beckenham; Roderick John Flower, London, both of England; Sergio Henrique Ferreira, Sao Paulo, Brazil

[73] Assignee: Burroughs Wellcome Co., Research Triangle Park, N.C.

[21] Appl. No.: 583,458

[22] Filed: Jun. 3, 1975

[30] Foreign Application Priority Data

Jun. 4, 1974 [GB] United Kingdom ............... 24660/74
Dec. 13, 1974 [GB] United Kingdom ............... 53986/74

[51] Int. Cl.$^2$ .................... A61K 39/00; A61K 31/215 A61K/31/19
[52] U.S. Cl. ........................................ 424/85; 424/88; 424/177; 424/305; 424/317
[58] Field of Search ................... 424/88, 85, 177, 317, 424/305

[56] References Cited

U.S. PATENT DOCUMENTS

| | | | |
|---|---|---|---|
| 3,690,834 | 9/1972 | Goldstein et al. | 23/230 R |
| 3,935,074 | 1/1976 | Rubenstein et al. | 424/12 |

OTHER PUBLICATIONS

Sato, et al.–Chem. Abst. vol. 81 (1974), pp. 150,209 m.
Gross–Chem. Abst. vol. 80 (1974), pp. 144,351 q.
Jaffe, et al.–Science vol. 171 (Feb. 5, 1971), pp. 494–496.

*Primary Examiner*—Sam Rosen
*Attorney, Agent, or Firm*—Donald Brown

[57] ABSTRACT

Immunogenic conjugates of prostaglandins of the A, B, D and E series and their structural analogues of value in the proplylaxis or therapy in mammals of pathological conditions in which prostaglandins are involved. Also provided are pharmaceutical formulations comprising the conjugates together with a carrier therefor and methods for the treatment of mammals comprising the administration thereto of a conjugate or formulation thereof.

22 Claims, No Drawings

CONJUGATES OF PROSTAGLANDINS, ANALOGS, FORMULATIONS AND THEIR USE

This invention relates to conjugates of prostaglandins and prostaglandin analogues, to the preparation of such conjugates, to pharmaceutical formulations which comprise such a conjugate, and to methods of therapy or prophylaxis in mammals which comprise the administration to a mammal of such a conjugate or such a formulation.

It has surprisingly been found that administration to a mammal of a prostaglandin conjugate of formula (I) as hereinafter defined effects an alleviation in the mammal of an experimentally induced pathological lesion, indicating the value of the conjugates in the prophylaxis or therapy in mammals (for example man, horse, cow, sheep) of pathological conditions in which prostaglandins are involved. In particular it has been found that administration to rats of a conjugate of prostaglandin $E_1$ ($PGE_1$) effects a reduction in the paw oedema consequent upon subplantar injection of carrageenin as compared with control animals which did not receive the conjugate.

The present invention more particularly relates to conjugates of prostaglandins (as hereinafter defined) of the general formula $\overline{(PG)}$-COOH, where $\overline{(PG)}$- represents that part of the prostaglandin molecule other than the terminal carboxyl group, with an immunogenic macromolecule containing a reactive free amino group, of the general formula $H_2N$- $\overline{(M)}$ where $\overline{(M)}$ -represents that part of the macromolecule other than the reactive free amino group. The prostaglandin and the macromolecule may be conjugated directly, by a peptide bond between their respective carboxyl and amino groups, or via an intermediate linking group (as hereinafter defined).

The prostaglandins (PGs) to which this invention relates and from which the conjugates may be formed include particularly those of the A series ($PGA_1$, $PGA_2$); the B series ($PGB_1$, $PGB_2$); the D series ($PGD_1$, $PGD_2$, $PGD_3$); and the E series $PGE_1$, $PGE_2$, $PGE_3$). However, this invention should be understood to relate also to conjugates prepared from analogues of the prostaglandins specifically recited above which retain the characteristic cyclopentane or cyclopentene group, or in which this group is replaced by a cyclohexane group.

Thus one class of prostaglandins and analogues thereof to which this invention relates and from which the conjugates may be formed comprises the compounds of the formula

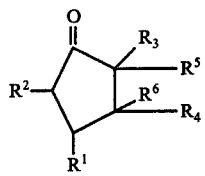

wherein
$R^1$ is hydrogen or hydroxy and $R^2$ is hydrogen, or $R^1$ and $R^2$ together form a bond;
$R^3$ and $R^4$ together form a bond when $R^1$ is hydrogen and are otherwise both hydrogen; and
one of $R^5$ and $R^6$ is a group $-X^1.COOH$ and the other is a group $-X^2.CH_3$, wherein $X^1$ and $X^2$ are the same or different and are each a carbon atom chain, preferably 2 to 8, more preferably 4 to 7 and optimally 6 or 7 carbon atoms in length.

The immunogenic macromolecule $H_2N\text{-}\overline{(M)}$ may be for example keyhole limpet haemocyanin but is preferably a protein such as gelatin or a protein fraction of a mammalian serum, for example a globulin ($\alpha,\beta$ or $\gamma$) or an albumin, where the mammalian species may be for example man, horse, cow or sheep. The "reactive free amino group" of the macromolecules specifically recited above is the $\mu$-amino group of a lysine residue in the macromolecule. Where the macromolecule includes a plurality of such residues it is thus possible to have in the conjugate a plurality of prostaglandin moieties, which may be the same or different, although in practice the free amino groups will not all be equally reactive and equally available for conjugation. For example the bovine serum albumin macromolecule is believed to include 88 lysine residues and thus has 88 free amino groups, but of these it is believed that only about 30 to 40 will permit of conjugation. Thus in the following Example 1 there is detailed the preparation of a bovine serum albumin-$PGE_1$ conjugate containing (on average) 9.6 moles of $PGE_1$ per mole of albumin. By varying for example the molar proportions of the prostaglandin and albumin in the reaction mixture (vid. inf.) conjugates may be obtained wherein this ratio (prostaglandin to albumin) is 1:1, 20:1, 30:1 or even greater.

The human serum albumin macromolecule is believed to include 84 lysine residues of which possibly only 40 or so are available for conjugation. The human $\gamma$-globulin (IgG) macromolecule is believed to include 55 lysine residues.

Where the conjugate includes a linking group this is desirably not too hydrophobic in nature and thus should not include excessively long unbroken hydrocarbon chains. A convenient class of linking group may be represented by the general formula

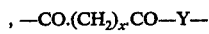
, $-CO.(CH_2)_x.CO-Y-$ wherein $x$ is 2 to 4 and Y is selected from
(i) $-NH(CH_2)_a NH-$ wherein $a$ is 2 to 6, preferably 2 to 4;
(ii) $-NH(CH_2)_{b^1}.Z.(CH_2)_{b^2}.NH-$ wherein $b^1$ and $b^2$ are the same or different but preferably the same and each is 1 to 4, preferably 2 to 4, and Z is $-O-$, $-NH-$ or $-CH(OH)-$;
(iii) $-W.CO.CH_2.W^1-$ wherein W and $W^1$ are the same or different and each is a group defined in (i) or (ii) above; and
(iv) $-NH.CH_2.CONH.CH_2.CO.W^2-$ wherein $W^2$ is a group defined in (i) or (ii) above.

With reference to the formula above the macromolecule and prostaglandin moieties are joined via peptide bonds to respectively the left-hand and right-hand functions of the linking group and the interrelation of the linking group and the macromoleucle and prostaglandin moieties may be represented in the form

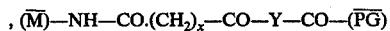
, $\overline{(M)}-NH-CO.(CH_2)_x-CO-Y-CO-\overline{(PG)}$

The conjugates to which this invention relates may be prepared by any method known in the art for, the preparation of compounds of analogous structure. Because of the acknowledged instability of the prostaglandins however their manipulation in the course of conjugation should be as limited as possible and hence in any multistage process (for example the preparation of a conjugate wherein there is a linking group) they should most desirably be introduced at the final stage.

Thus preparation of a conjugate which includes a linking group (as above defined) may comprise the sequence of steps (a) Preparation of the derivative (A)

$$\overline{(M)}-NH-CO.(CH_2)_x COOH \quad (A)$$

from the macromolecule $\overline{(M)}-NH_2$, for example by reaction with the appropriate acid anhydride $(CO(CH_2)_x. CO)O$ (b) Preparation from (A) of the derivative (B)

$$\overline{(M)}-NH-CO.(CH_2)_x.CO.Y-H \quad (B)$$

by reaction with the appropriate bis-amine H—Y-H (c) Coupling with (B) of the appropriate prostaglandin $\overline{(PG)}$-COOH, or with a mixture of prostaglandins, to yield the final conjugate.

In the foregoing all symbols have the values indicated for them hereinabove. When the group —Y— has the value —W—CO.CH$_2$—W$^1$— the appropriate derivative (B) as above illustrated may also be prepared by initially forming the derivative $\overline{(M)}-NH.CO.(CH_2)_x.CO.W-H$ from the corresponding derivative (A) and the bis-amine H-W-H, reacting this with the N-hydroxy succinimido ester of bromacetic acid to give the activated derivative $$, \overline{(M)}-NH.CO.(CH_2)_x.CO.W.CO.CH_2Br$$

and reacting this with the appropriate bis-amine H—W-$^1$—H.

When the group —Y— has the value —NH.CH$_2$.CONH.CH$_2$.CO.W$^2$—the appropriate derivative (B) may also be prepared by coupling the appropriate derivative (A) with glycylglycine (NH$_2$.CH$_2$.CONH.CH$_2$.COOH) to yield $$, \overline{(M)}-HN.CO.(CH_2)_x.CO.NH.CH_2.COHN.CH_2.COOH$$

and reacting this with the appropriate bis-amine —H—w$_2$—H.

The preparation of the those conjugates wherein the prostaglandin and macromolecule moieties are linked directly, as well as the appropriate steps as above described in the preparation of conjugates including a linking group, are preferably effected using one of the procedures known in the art to promote peptide bond formation, for example by the use of a carbodiimide, by the use of Woodward's reagent K, or by the mixed anhydride method. If a cartodiimide is employed it is most preferably one such as, for example, N-(3-dimethylaminopropyl)-N-ethylcarbodiimide and N-(3-diethylaminopropyl)-N-ethylcarbodiimide whereof the corresponding urea, a byproduct in the reaction, is water-soluble and thus may be dialysed out from the reaction mixture. Suitable reagents for the mixed anhydride method include ethylchloroformate, isobutylchloroformate and isobutylchlorocarbonate and the reaction is desirably carried out in the presence of a tertiary organic base such as a trialkylamine, for example triethylamine or tri-n-butylamine, or N-methylmorpholine. Woodward's reagent K is N-ethyl-5-phenylisoxazolium-3'-sulphonate.

In the preparation of those conjugates having a linking group, condensation of the prostaglandin $\overline{(PG)}$-COOH is possible both with the newly created amino function (resulting from incorporation of the bis-amine H—Y—H) and with any of the original amino functions of the starting material $\overline{(M)}.NH_2$ that are still reactive and free. In the initial step (q.v.) therefore sufficient of the acid anhydride is present to ensure reaction therewith of all the reactive free amino groups. A 12-fold molar excess of anhydride over the total number of amino groups is suitable, and where the macromolecule $\overline{(M)}-NH_2$ includes tyrosine residues (as does e.g. bovine serum albumin) this step is desirably carried out at a slightly alkaline pH such as pH 8.0 to avoid acylation of the tyrosine hydroxyl groups.

Condensation of the bis-amine H—Y—H will occur not only with the newly created carboxyl function (resulting from the acid anhydride) but also with any free and reactive carboxyl functions (from aspartic acid and glutamic acid residues) in the starting material $\overline{(M)}-NH_2$. Bovine serum albumin, human serum albumin and human γ-globulin (IgG) are all known to contain free carboxyl functions of this type and it may be assumed that at least some of these will be reactive and available for condensation. This bis-amine H—Y—H should most desirably be present in very large excess in order to avoid cross-linking of the product.

The conjugates to which this invention relates may thus be represented by formula (I)

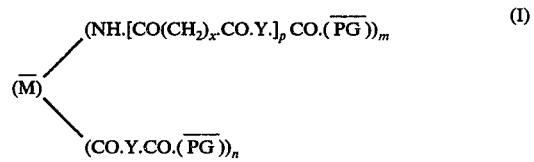

wherein $\overline{(M)}$, $\overline{(PG)}$, Y and x are as hereinbefore defined, m is at least 1 and is not greater than the number of free amino groups in the parent macromolecule of the group $\overline{(M)}$ available for acylation;

p is 0 or 1;

n is 0 or an ingeger not greater than the number of carboxyl groups in the parent macromolecule of the group $\overline{(M)}$ available for reaction with the bis-amine H—Y—H, and is 0 when p is 0;

and where, when the sum of m and n is greater than 1 the groups $\overline{(PG)}$ may be the same or different.

These conjugates may be prepared by reacting the appropriate amine

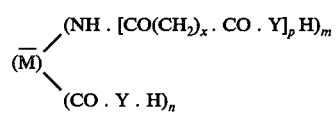

with the appropriate prostaglandin $\overline{(PG)}$.COOH or a mixture of different prostaglandins.

It is believed that all of the conjugates of formula (I) as above defined are novel with the exception of those wherein p and n are both 0 and which include only one species of group $\overline{(PG)}$ derived from a prostaglandin selected from A$_1$, A$_2$, B$_1$, E$_1$ and E$_2$. None of the conjugates within formula (I) that are known have been ascribed any utility in human or veterinary medicine.

Until required for use the conjugates of formula (I) are desirably stored in the freeze-dried stated to minimise possible degradation of the prostaglandin moeity.

As mentioned above the conjugates of formula (I) are of value in the prophylaxis or therapy in mammals of pathological medical or veterinary conditions in which prostaglandins are involved, and the precise field of utility of any conjugate will depend upon the prostaglandin moiety thereof. Thus those conjugates in which the prostaglandin moiety is of the E series ($PGE_1$; $PGE_2$; $PGE_3$) have particular utility in the prophylaxis or therapy, but more particularly therapy, of the conditions listed below.

(a) Diseases where there are acute or chronic inflammatory changes without direct infective cause, eg. ulcerative colitis, collagenoses, connective tissue disturbances, non-infective arthritides, peri-articular disorders including particularly rheumatold arthritis, gout, and degenerative arthritis.

(b) Conditions with acute or chronic inflammatory changes primarily due to allergic or immunological causes such as allergic rhinitis, urticaria, eczema and other allergic skin diseases, and inflammatory conditions of the eye.

(c) Disorders due to blood platelet aggregation.

These conjugates also have particular utility in the prophylaxis or therapy, but more particularly prophylaxis, of (d) Migraine and related conditions.

Due to the structural similarity of the prostaglandins of the A, B, D and E series, wherein in each case there is an oxo group in the 9- or 11-position (using the conventional numbering system for prostaglandins) conjugates wherein the prostaglandin portion (s) is of the A, B or D series, together with structural analogues of prostaglandins of the A, B, D or E series which retain the characteristic cyclopentane or cyclopentene ring, also have utility as indicated above in the conditions above described.

The macromolecule moiety of a conjugate is desirably nonantigenic in the species to which it is intended the conjugate be administered, and thus those conjugates intended for administration to man are most suitably derived from a human serum protein fraction such as human serum albumin or a human serum globulin.

The conjugates may be administered in any manner known to be suitable for the production of active immunity, but conveniently by subcutaneous, intradermal or intramuscular injection. In general the amount required by a mammal of a conjugate of formula (I) for the production of active immunity will lie in the range 1 to 1000μg (calculated as the prostaglandin moiety) per kilogram bodyweight, this dose to be repeated as necessary in accordance with any appropriate immunization schedule.

The conjugates are preferably administered as a pharmaceutical vaccine formulation which is preferably sterile and which comprises, both for veterinary and for human medical use, a conjugate of formula (I) (hereinafter referred to as the active ingredient) together with one or more acceptable carriers therefor. The carrier(s) must be "acceptable" in the sense of being compatible with the other ingredients of the formulation and not deleterious to the recipient thereof. The formulations may conveniently be presented in unit dosage form, for example as sealed ampoules each holding a known amount of active ingredient, and may be prepared by bringing into association the active ingredient with the carrier(s) therefor. Where the formulation is sterile this may be effected by individual sterilization of the components of the formulation prior to their admixture under sterile conditions, or by sterilization of the formulation itself, using any of the appropriate techniques known in the art.

Suitable formulations include aqueous suspensions of the active ingredient and (when the active ingredient is water-soluble as when derived from a serum albumin) aqueous solutions, where the aqueous medium is for example pyrogen-free water or physiological saline, and such suspensions and solutions may be prepared as required by addition of the aqueous medium to the powered, optionally freeze-dried active ingredient. Advantageously however the formulations include an adjuvant for enhancing the immune response to the active ingredient. Suitable adjuvants include (a) aluminium or calcium salts, for example potash alum and calcium phosphate; (b) a vegetable oil (for example peanut oil) or a mineral oil, when the formulation also includes a suitable emulsifying agent and may be presented as an oil-in-water or water-in-oil emulsion; (c) a killed bacterial suspension, for example where the bacteria are *Corynebacterium parvum*; and (d) (except where the resultant formulation is for administration to man) Freund's adjuvant, either complete or incomplete.

As further examples of suitable adjuvants may be mentioned:

BCG (Bacille-Calmette-Guerin)
Alluminium hydroxide (alhydrogel)
Arquad 2HT (dioctadecyl dimethyl ammonium chloride)
Adjuvant 65 (Merck)

In addition to the ingredients mentioned above the formulations may include one or more additional ingredients such as buffers, preservatives (including anti-oxidants), and materials included to render the formulations isotonic with the blood of the intended recipient.

It will be appreciated that while an immediate utility of the conjugates of formula (I) is in the active immunization of mammals, as hereinbefore described, the conjugates are also of value in thus enabling the raising of immunoglobulins which may be used in the passive immunization of animals of the same or of a different mammalian species from that in which the immunoglobulins were raised. For example immunoglobulins raised in a horse or in man by active immunization with a conjugate of formula (I) may be used in the passive immunization of other humans. Such materials may be administered as sterile aqueous preparations which may be prepared as required by addition of the aqueous medium to the powdered solid. They may be administered by any method known in the art to be suitable and conveniently by intramuscular injection.

Immunoglobulins raised by active immunization with a conjugate in which the prostaglandin moiety is of the E series ($PGE_1$; $PGE_2$; $PGE_3$) have particularly utility in passive immunization in the following circumstances:

(a) the management of acute or chronic inflammatory conditions of infective origin where the control of the effects of infection is of particular importance;

(b) in certain circumstances in the control of postoperative inflammatory responses;

(c) the control of pyrexia.

The following Examples are provided by way of nonlimiting illustration.

EXAMPLE 1

(a) Preparation of the bovine serum albumin - PGE₁ conjugate

PGE₁ (20 mg) was dissolved in 0.02% (w/v) sodium carbonate solution in 10% aqueous ethanol (20 ml). To this solution were added bovine serum albumin (46 mg) and N-(3-dimethylaminopropyl)-N-ethylcarbodiimide hydrochloride (20 mg) and the resulting mixture was stirred at ambient temperature (24 hrs.). The mixture was then dialysed (4° C, 24 hrs.) using Visking tubing 24/32 against the buffer (0.005M disodium hydrogen phosphate/sodium dihydrogen phosphate, pH 7.0; 0.15M sodium chloride) at pH 7.2 (four changes each of 500 ml). The solid (315 mg) obtained by lyophilisation was shown spectroscopically (U.V.) to contain ca. 2.06 mg $PGE_1$ (ie. ca. 9.6 moles of $PGE_1$ per mole of bovine serum albumin) by measurement of the molar extinction coefficient of the prostaglandin portion of the conjugate. ($E_m$ = 27,200).

(b) Immunization of Rats

Male Wistar rats (21) 3 weeks old were divided into two groups. One group was injected subdermally at monthly intervals (3 injections in toto) with the bovine serum albumin-$PGE_1$ conjugate (500μg) emulsified in Freund's complete adjuvant (0.1 ml), the control group being injected on the same timetable with Freund's complete adjuvant (0.1 ml) alone.

(c) Measurement of Antibody Titres

One month after the last injection two animals in each group (immunized and control) were anaesthetised (nembutal) and blood (2 ml) was withdrawn by cannulation of the descending aorta into a tube containing heparin (0.1 ml, 5000 units/ml). After gentle mixing the blood was centrifuged (5000g; 20 min) and the plasma removed and diluted with TRIS (tris(hydroxymethyl-)aminomethane)-hydrochloric acid buffer (pH 7.5; 100 mM) to give 1:2 and 1:5 dilutions. 0.5 ml Aliquots of undiluted or diluted plasma in test tubes were mixed with $^3H$-$PGE_1$ (approx. $10^4$ c.p.m.; Radiochemicals, Amersham) and the tubes then incubated (4° C; 18 hrs.).

When incubation was complete polyethylene glycol 4000 (0.5ml; 25% (w/v) aqueous solution) was added, and the contents of the tubes mixed and transferred into cooled centrifuge tubes. After centrifugation (10,000g; 30 min) 0.1 ml of the supernatant was removed and the radioactivity of the sample estimated by liquid scintillation counting techniques. Comparison of this figure with the radioactivity initially added enabled calculation of the binding to the plasma, i.e. that (radioactively) labelled prostaglandin precipitated with the protein.

The results are set out in Table 1.

(d) Measurement of Inflammatory Response

This was done one month after the last injection of the conjugate. The animals, both immunized and control, were starved overnight and inflammation induced next day by subplantar injection in one paw of carrageenin (0.1 ml of a 0.5% solution in physiological saline). At the same time the contralateral (control) paw was injected in like manner with 0.1 ml physiological saline alone. The paw volume was measured by the mercury displacement method (Journal of Pharmacology and Experimental Therapeutics, 150, 328 (1965) and the increase consequent upon the induced inflammation was calculated by substracting the volume of the control paw from that of the paw injected with carrageenin.

The results are set out in Table 2 which shows the increase in paw volume over a period of 4 hours from the time of injection. The response (increase in volume) exhibited by the immunized animals was significantly less then that exhibited by the control animals.

EXAMPLE 2

Preparation of a bovine serum albumin - $PGE_1$ conjugate having an intermediate linking group.

(a) Succinylated bovine serum albumin (Suc-BSA)

Crystalline bovine serum albumin (5.0 g.) was dissolved in water (100 ml.) and the solution cooled to 0° C. Succinic anhydride (5.0 g.) was gradually, with stirring, added over a period of 1 hour, whilst maintaining the pH at 8.0 by the addition of N. sodium hydroxide (use pH-stat). After the addition of the anhydride the reaction was allowed to proceed for 30 minutes. A total of 98.6 ml. of N. sodium hydroxide was consumed. The solution was dialysed (Visking Tubing 36/32) at 4° C for 48 hours against frequent changes of distilled water. The contents of the tube were lyophilised to give 5.71g. of amorphous powder.

Ninhydrin assay as carried out by the method of E. W. Yemm and E. C. Cooking (Analyst, 1955, 80, 209) indicated that all the amino groups in the albumin had been succinylated.

(b) Reaction of Suc-BSA with 3,3¹-diaminodipropylamine

Succinylated bovine serum albumin (70 mg.) was dissolved in water (25 ml.). 3,3¹-Diaminodipropylamine dihydrochloride (1.59 g.) (ca. 50 fold excess over total carboxyl groups) and ethyldiethylaminopropylcarbodiimide hydrochloride (0.89 g.) (ca. 30 fold excess over total carboxyl groups) were added. The pH of the solution was adjusted to 5.0 with 0.5 N hydrochloric acid and the reaction mixture stirred in the dark at ambient temperature for 24 hours. The solution was dialysed (Visking tubing 18/32) at 4° C against frequent changes of distilled water. The contents of the tubing were lyophilised to give 80 mg. of a white amorphous powder. (DAP-Suc-BSA).

By ninhydrin assay the total amino groups was estimated to be 80.

(c) Conjugation of Prostaglandin $PGE_1$ with the DAP-Suc-BSA

Prostaglandin $PGE_1$ (30 mg.) was dissolved in ethanol containing 10% of 0.02% aqueous sodium carbonate (30 ml.) DAP-Suc-BSA (60 mg.) and ethyl diethylaminopropylcarbodiimide hydrochloride (30 mg.) were added. The pH was adjusted to 6.8 with 0.5N sodium carbonate solution and the mixture stirred at ambient temperature for 24 hours. The solution was dialysed (Visking tubing 18/32) at 4° C against 4 changes of buffer (0.005 M disodium hydrogen phosphate/sodium dihydrogen phosphate: 0.15 M. sodium chloride adjusted to pH 7.0 with N sodium hydroxide) over a period of 24 hours. The contents of the tubing were lyophilised to give 310 mg. of a white amorphous powder.

The $PGE_1$ content of the conjugate was estimated spectrophotometrically (see Example 1) to correspond to the presence of 10 moles of hapten per mole of modified protein, i.e. 10 of the available amino groups had been substituted by prostaglandin. This provided a formula:

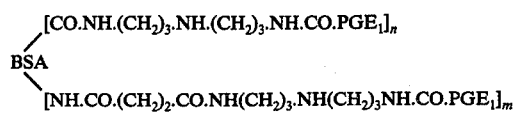

where $n + m = 10$

TABLE 1

Original $^3$H-PGE$_1$ (%) bound to plasma in rats immunized with the bovine serum albumin-PGE$_1$ conjugate.

| | Plasma | | |
|---|---|---|---|
| | Undiluted | Diluted | |
| | | 1:2 | 1:5 |
| * Control | 0 | 0 | 0.5 |
| * Immunized | 31 | 8 | 1 |

* Each figure is the mean of two rats

TABLE 2

Carrageenin - induced paw oedema in rats immunized with the bovine serum albumin-PGE$_1$ conjugate.

| | | | Increase of paw volume (μl) (m ± S.E.M.) (time post injection) | | | |
|---|---|---|---|---|---|---|
| | n | Weight (g) | 0hr. | 1hr. | 2hrs. | 4hrs. |
| Control | 10 | 359 (±12) | −4.1 (±14) | 348.2 (±59.0) | 568.8 (±54.2) | 785.9 (±40.5) |
| Immunized | 11 | 330 (±8.2) | 12.4 (±8.6) | 206.7 (±19.0) | 395.6 (±31.1) | 607.7 (±35.0) |
| p* | — | — | N.S. | p<0.05 | p<0.01 | p<0.005 |

*The significance between groups was analysed by the unpaired "t-test".
N.S. = not-significant.

EXAMPLE 3

Injectable Presentation of the Conjugate of Example 1

The dialysed mixture from Example 1 was assayed. This solution was then sterilised by filtration through a membrane filter, 0.22 μm pore size. Volumes of the sterile filtrate containing the equivalent of 5 mg of bovine serum albumin were distributed with aseptic precautions into previously sterilised vials and were freeze-dried. After this processing the vials were sealed with sterile rubber closures. The vaccine was retained in this freeze-dried state until required.

The injection was prepared by redissolving the freeze-dried materil in 1 ml of a sterile solution of sodium chloride 0.9% (w/v).

Alternatively, the injection was reconstituted by adding to one vial of the freeze-dried vaccine 0.2 ml of a sterile suspension of ultrafine hydrated alumina containing approximately 7.0 mg aluminium/ml (Alhydrogel prepared by Superfos Export Co., Copenhagen is suitable). This mixture was allowed to stand for a short period and diluted to 1 ml volume by the addition of sterile sodium chloride 0.9% (w/v) before administering by intramuscular or subcutaneous injection.

EXAMPLE 4

Injectable Presentation of the Conjugate of Example 2

The dialysed mixture from Example 2 was assayed. This solution was then sterilised by filtration through a membrane filter, 0.22 μm pore size. Volumes of the sterile filtrate containing the equivalent of 1 mg conjugate were distributed into previously sterilised vials and were freeze-dried and sealed as for Example 3. This vaccine was reconstituted in the same manner as detailed in Example 3.

What we claim is:

1. A conjugate of formula (I)

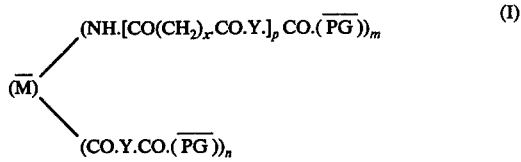

wherein $\overline{(M)}$ is that part of the macromolecule other than the reactive free amino group of an immunogenic macromolecule of the formula $\overline{(M)}-NH_2$:

$\overline{(PG)}$ is the residue of a prostaglandin or analogue thereof of the formula $\overline{(PG)}$-COOH selected from prostaglandins of the A, B, D and E series and those analogues thereof wherein there is retained the characteristic cyclopentane or cyclopentene group or wherein this group is replaced by a cyclohexane group;

Y is selected from
 (i) $-NH(CH_2)_aNH-$ where $a$ is 2 to 6;
 (ii) $-NH(CH_2)_{b1}.Z.(CH_2)_{b2}.NH-$ where $b1$ and $b2$ are the same or different and each is 1 to 4 and Z is $-O-$, $-NH-$ or $-CH(OH)-$;
 (iii) $-W.CO.CH_2.W^1-$ where W and $W^1$ are the same or different and each is a group defined in (i) or (ii) above; or
 (iv) $-NH.CH_2.CONH.CH_2.CO.W^2-$ where $W^2$ is a group defined in (i) or (ii) above;

$x$ is 2 to 4;

$m$ is at least 1 and is not greater than the number of free amino groups in the parent macromolecule of the group $\overline{(M)}$ available for acylation;

$p$ is 1; and $n$ is 0 or an integer not greater than the number of carboxyl groups in the parent macromolecule of the group $\overline{(M)}$ available for reaction with the bis-amine H-Y-H;

and where, when the sum of m and n is greater than 1 the groups $\overline{(PG)}$ may be the same or different.

2. A conjugate according to claim 1, wherein Y is $-NH(CH_2)_{b1}.Z.(CH_2)_{b2}.NH-$ where Z is $-NH-$ and $b^1$ and $b^2$ are the same or different and each is 2 to 4, or Y is $-NH(CH_2)_aNH-$ where $a$ is 2 to 4.

3. A conjugate according to claim 1 wherein $\overline{(PG)}$ is derived from a compound of the formula

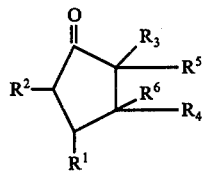

wherein
 $R^1$ is hydrogen or hydroxy and $R^2$ is hydrogen, or $R^1$ and $R^2$ together form a bond;
 $R^3$ and $R^4$ together form a bond when $R^1$ is hydrogen and are otherwise both hydrogen; and
 one of $R^5$ and $R^6$ is a group $-X^1.COOH$ and the other is a group $-X^2.CH_3$ where $X^1$ and $X^2$ are the same or different and are each a carbon atom chain.

4. A conjugate according to claim 3, wherein $\overline{(PG)}$ is derived from a compound defined in claim 3 wherein $X^1$ and $X^2$ are each 2 to 8 carbon atoms in length.

5. A conjugate according to claim 3, wherein $\overline{(PG)}$ is defined in claim 3 wherein $X^1$ and $X^2$ are each 6 or 7 carbon atoms in length.

6. A conjugate according to claim 1, wherein $\overline{(M)}$ is derived from a protein fraction of a mammalian serum.

7. A conjugate according to claim 1, wherein $\overline{(M)}$ is derived from a protein fraction of human serum.

8. A conjugate according to claim 1 wherein $\overline{(M)}$ is derived from human serum albumin.

9. A conjugate according to claim 1, wherein $x$ is 2.

10. A conjugate according to claim 1, wherein $\overline{(PG)}$ is derived from a prostaglandin of the E series.

11. A conjugate according to claim 1, wherein the sum of $m$ and $n$ is greater than 1 and the groups $\overline{(PG)}$ are different.

12. A conjugate according to claim 1, wherein Y is $-NH(CH_2)_3.NH.(CH_2)_3NH-$.

13. A pharmaceutical formulation suitable for parenteral administration in the prophylaxis or therapy in mammals of a pathological condition in which endogenous prostaglandins are involved, which comprises an effective prophylactic or therapeutic amount of a conjugate of formula (I) as defined in claim 1 together with an adjuvant therefor.

14. A formulation according to claim 13 wherein the adjuvant is acceptable in man.

15. A a formulation according to claim 13 wherein the adjuvant is aluminium hydroxide.

16. A formulation according to claim 13 which is a solution or suspension in an aqueous liquid medium.

17. A sealed ampoule containing a known unit dosage amount of a formulation according to claim 13.

18. An ampoule according to claim 17 wherein the contents are in the freeze-dried state.

19. A method for the therapy or prophylaxis in a human of a pathological condition in which endogenous prostaglandins are involved, comprising parenteral administration to the human of an effective therapeutic or prophylactic amount of a conjugate of formula (I)

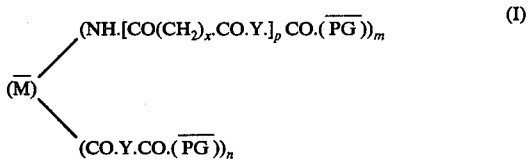

wherein
$\overline{(M)}$ is that part of the macromolecule other than the reactive free amino group of an immunogenic macromolecule of the formula $\overline{(M)}-NH_2$;

$\overline{(PG)}$ is the residue of a prostaglandin or analogue thereof of the formula $\overline{(PG)}$-COOH selected from prostaglandins of the A, B, D and E series and those analogues thereof wherein there is retained the characteristic cyclopentane or cyclopentene group or wherein this group is replaced by a cyclohexane group;

Y is selected from
(i) $-NH(CH_2)_a NH-$ where $a$ is 2 to 6;
(ii) $-NH(CH_2)_{b1}.Z.(CH_2)_{b2}.NH-$ where $b1$ and $b2$ are the same or different and each is 1 to 4 and Z is -O-, -NH- or $-CH(OH)-$;
(iii) $-W.CO.CH_2.W^1-$ where W and $W^1$ are the same or different and each is a group defined in (i) or (ii) above; or
(iv) $-NH.CH_2.CONH.CH_2.CO.W^2-$ where $W^2$ is a group defined in (i) or (ii) above;

$x$ is 2 to 4;

$m$ is at least 1 and is not greater than the number of free amino groups in the parent macromolecule of the group $\overline{(M)}$ available for acylation;

$p$ is 0 or 1; and $n$ is 0 or an integer not greater than the number of carboxyl groups in the parent macromolecule of the group $\overline{(M)}$ available for reaction with the bis-amine H—Y—H, and is 0 when $p$ is 0;

and where, when the sum of $m$ and $n$ is greater than 1 the groups $\overline{(PG)}$ may be the same or different.

20. A method according to claim 19 wherein the conjugate is administered to the human in an amount in the range (calculated as the prostaglandin moiety in the conjugate) 21 to 1000 µg per kilogram bodyweight.

21. A method for the therapy or prophylaxis of inflammation in a human comprising parenteral administration to the human of an effective inflammation therapeutic or prophylatic amount of a conjugate of formula (I) defined in claim 19.

22. A method of raising antibodies in a human comprising parenteral administration to the human of an effective antibody-raising amount of a conjugate of formula (I) defined in claim 19.

* * * * *